(12) United States Patent
Malladi et al.

(10) Patent No.: US 6,355,814 B1
(45) Date of Patent: Mar. 12, 2002

(54) PROCESS FOR THE PREPARATION OF 3-HYDROXYMETHYL TETRAHYDROFURAN

(75) Inventors: Pardhasaradhi Malladi; Sri Nagesh Kumar Potluri, both of Andhra Pradesh (IN)

(73) Assignee: Council of Scientific and Industrial Research of India, New Delhi (IN)

( * ) Notice: Subject to any disclaimer, the term of this patent is extended or adjusted under 35 U.S.C. 154(b) by 0 days.

(21) Appl. No.: 09/796,085

(22) Filed: Feb. 28, 2001

(51) Int. Cl.$^7$ .............................................. C07D 307/12
(52) U.S. Cl. ........................ 549/497; 549/508; 549/509
(58) Field of Search ................................ 549/497, 508, 549/509

(56) References Cited

U.S. PATENT DOCUMENTS 4,089,871 A * 5/1978 Lillwitz .................... 260/347.8
5,912,364 A * 6/1999 Beavers ....................... 549/429

* cited by examiner

Primary Examiner—Ba K. Trinh
(74) Attorney, Agent, or Firm—Darby & Darby

(57) ABSTRACT

The present invention relates to a catalytic process for the preparation of 3-hydroxymethyl tetrahydrofuran of formula IV

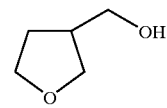

Formula IV with hydroformylation as one of the key steps. The process comprises reacting 9-hydroxymethyl-7,12-dioxaspiro[5,6] dodecane of the formula III

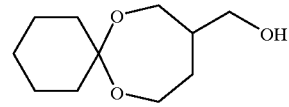

Formula III with an alcohol in the presence of an acid catalyst and recovering the 3-hydroxymethyl tetrahydrofuran.

4 Claims, No Drawings

PROCESS FOR THE PREPARATION OF 3-HYDROXYMETHYL TETRAHYDROFURAN

FIELD OF THE INVENTION

The present invention relates to a process for the preparation of 3-hydroxymethyl tetrahydrofuran. The present invention particularly relates to a catalytic process for the preparation of 3-hydroxymethyl tetrahydrofuran with hydroformylation as one of the key steps.

BACKGROUND OF THE INVENTION 3-hydroxymethyl tetrahydrofuran is an important intermediate in the synthesis of drugs and pesticides. The guanidine derivatives derivable from 3-hydroxymethyl tetrahydrofuran have assumed greater significance as pesticides in recent years. (JP 07 173,157; U.S. Pat. No. 5,382,596; JP 08 245,323; JP 08 245,32; JP 08 259,568, JP 08, 259,554, JP 08 259,553; JP08 269,035; JP 08 291,009; JP 08 269,034; JP 08 295,684; JP 08 291,169; JP 08 291,171; JP 08 311,063; U.S. Pat. No. 5,585,397; JP 09 12,565; EP 0649845).

In the art, it is known to prepare 3-hydroxymethyl tetrahydrofuran by dehydration of 2-hydroxymethyl-1,4-butanediol in the presence of phosphoric acid. 2-hydroxymethyl-1,4-butanediol was prepared by reduction of 2-carboethoxy diethyl succinate using $LiBH_4$ [C.R.Acad. Sci., Paris, Ser. C264(10), 894-6(1967) (Fr)]. This procedure has the disadvantage of using large quantities of $LiBH_4$ to effect reduction of the esters to the corresponding alcohol. Since 2-hydroxymethyl-1,4-butanediol is highly soluble in water, this method also has the disadvantage of requiring isolation of the triol from aqueous solutions during work up. Recently in 1997 a process for the preparation of 3-hydroxymethyl tetrahydrofuran was reported by cyclocondensation of 2-bydroxymethyl-1,4-butanediol using para toluenesulphonic Acid, [JP 08,291,159, CA 126:74732], This process has the disadvantage of prior separation of soluble para toluene sulphonic acid from the reaction mixture, before 2-bydroxymethyl tetrahydrofuran is isolated either by solvent extraction and/or distillation. The reactions involved in procedures mentioned above are all stiochiometric reactions.

In view of these disadvantages it is felt highly desirable to develop a practical process for the preparation of 3-hydroxymethyl tetrahydrofuran. It is also felt necessary to develop a process, in which salt generation is kept at minimum, to make it environmentally friendly. The process thus developed will have the advantage of being catalytic and free of salt generation.

OBJECTS OF THE INVENTION

The main object of the present invention is to provide a process for the preparation of 3-hydroxymethyl tetrahydrofuran of the formula IV starting from cyclohexanone and but-2-ene-1,4-diol.

It is another object of the invention to provide a process for the preparation of 3-hydroxymethyl tetrahydrofuran wherein salt generation is minimised thereby making the process more environmentally friendly.

SUMMARY OF THE INVENTION

Accordingly the present invention provides a process for the preparation of 3-hydroxymethyl tetrahydrofuran of the formula IV,

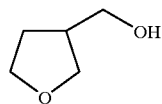

Formula IV said process comprising reacting 9-hydroxymethyl-7,12-dioxaspiro dodecane of the formula III

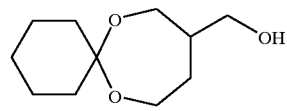

Formula III with an alcohol at a temperature in the range of 100–140° C. for a time period in the range of 1–4 hr. in the presence of an acid catalyst and recovering the 3-hydroxymethyl tetrahydrofuran.

In one embodiment of the invention the alcohol used contains 1 to 4 carbon atoms and is selected from the group consisting of methanol, ethanol, propanol and butanol.

In another embodiment of the invention the acid catalyst used comprises a heterogeneous acid catalysts.

In a further embodiment of the invention, the acid catalyst used is selected from the group consisting of amberlyst-15, Montmorillonite K-10 and Sulphonated Nitro Coal Acid (SNCA).

DETAILED DESCRIPTION OF THE INVENTION

The process of the present invention is detailed below.

7,12-dioxaspiro[5,6]dodec-9-ene of the formula I obtained by reacting cyclohexanone with but-2-ene-1,4-diol was hydroformylated using Rhodium catalyst to give 9-formyl-7,12-dioxaspiro[5,6]dodecane of the formula II. 9-hydroxymethyl-7,12-dioxaspiro[5,6]dodecane of the formula III obtained by reduction of formyl group was subjected to simultaneous transketalisation and cyclodehydration to give 3-hydroxymethyl tetrahydrofuran of the formula IV in the presence of a heterogeneous acid catalyst. The product 3-hydroxymethyl tetrahydrofuran was distilled after filtration of the catalyst. The entire process of the reaction is detailed in the reaction scheme below:

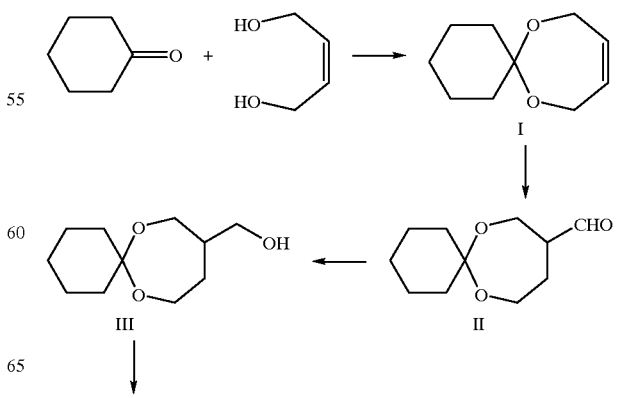

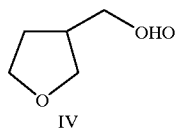

IV

U.S. Pat. No. 5,864,046 granted to Pardhasaradhi et al discloses the preparation of 9-hydroxymethyl-7,12-dioxaspiro[5,6]dodecane of the formula III via hydroformylation followed by reduction starting from cyclohexanone and but-2-ene-1,4-diol.

The following examples are given by way of illustrations of the present invention and therefore, should not be construed to limit the scope of the present invention.

EXAMPLE 1

A mixture of 9-hydroxymethyl-7,12-dioxaspiro[5,6] dodecane (10 g), butanol (20 ml) and montmorillonite K-10 (1 g) was heated to 100° C. and butanol distilled off. The reaction temperature was raised to 120° C. and heated for 30 min. The catalyst was filtered and the product isolated by distillation at 92° C./7 torr to provide 3-hydroxymethyl tetrahydrofuran of the formula IV (70%).

EXAMPLE 2

A mixture of 9-hydroxymethyl-7,12-dioxaspiro[5,6] dodecane (10 g) in ethanol (20 ml) and Amberlyst-15 (1 g) was heated under reflux and ethanol distilled out. It was heated to 120° C. and maintained for 30 min. The catalyst was filtered and the residue distilled at 92° C./7 torr to give 3-hydroxymethyl tetrahydrofuran of the formula IV (87%).

EXAMPLE 3

A mixture of 9-hydroxymethyl-7,12-dioxaspiro[5,6] dodecane (10 g), methanol (20 ml) and Amberlyst-15 (1 g) was heated under reflux and methanol distilled out. It was heated to 120° C. and maintained for 30 min. The catalyst was filtered and the residue distilled at 92° C./7 torr to give 3-hydroxymethyl tetrahydrofuran of the formula IV (90%).

EXAMPLE 4

A solution of 9-hydroxymethyl-7,12-dioxaspiro[5,6] dodecane (10 g) in methanol (20 ml) and Sulphonated Nitro Coal Acid (SNCA) (1 g) was heated to reflux and methanol distilled out. It was heated to 120° C. and maintained for 30 min. The catalyst was filtered and the residue distilled at 92° C./7 torr to give 3-hydroxymethyl tetrahydrofuran of the formula IV (75%).

EXAMPLE 5

A mixture of 9-hydroxymethyl-7,12-dioxaspiro[5,6] dodecane (10 g) in propanol (20 ml) and Amberlyst-15 (1 g) was heated under reflux and propanol distilled out. It was heated to 120° C. and maintained for 30 min. The catalyst was filtered and the residue distilled at 92° C./7 torr to give 3-hydroxymethyl tetrahydrofuran of the formula IV (87%).

EXAMPLE 6

A solution of 9-hydroxymethyl-7,12-dioxaspiro[5,6] dodecane (10 g) in propanol (20 ml) and Sulphonated Nitro Coal Acid (SNCA) (1 g) was heated to reflux and propanol distilled out. It was heated to 120° C. and maintained for 30 min. The catalyst was filtered and the residue distilled at 92° C./7 tour to give 3-hydroxymethyl tetrahydrofuran of the formula IV (78%).

EXAMPLE 7

A mixture of 9-hydroxymethyl-7,12-dioxaspiro[5,6] dodecane (10 g), propanol (20 ml) and montmorillonite K-10 (1 g) was heated to 100° C. and propanol distilled off. The reaction temperature was raised to 120° C. and heated for 30 min. The catalyst was filtered and the product isolated by distillation at 92° C./7 torr to provide 3-hydroxymethyl tetrahydrofuran of the formula IV (70%).

EXAMPLE 8

A mixture of 9-hydroxymethyl-7,12-dioxaspiro[5,6] dodecane (10 g), butanol (20 ml) and Sulphonated Nitro Coal Acid (1 g) was heated to 100° C. and butanol distilled off. The reaction temperature was raised to 120° C. and heated for 30 min. The catalyst was filtered and the product isolated by distillation at 92° C./7 torr to provide 3-hydroxymethyl tetrahydrofuran (73%).

The advantages of the present invention are:
1. The process consists of mostly catalytic reactions in which salt formation is at the minimum.
2. Cyclohexanone is recovered and reused in the process.
3. Because of the usage of heterogeneous acid catalyst the process does not require water wash on the other hand, the heterogeneous catalysis is simply filtered and the product distilled.
4. The process is suitable for commercial exploitation because of the high yields in each step and the usage of cheap raw materials like cyclohexanone and but-2-ene-1, 4-diol and syngas.

We claim:

1. A process for the preparation of 3-hydroxymethyl tetrahydrofuran of the formula IV,

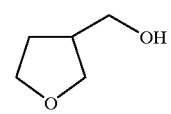

Formula IV said process comprising reacting 9-hydroxymethyl-7,12-dioxaspiro dodecane of the formula III.

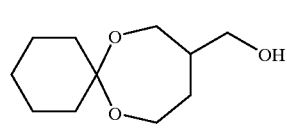

Formula III with an alcohol at a temperature in the range of 100–140° C. for a time period in the range of 1–4 hr. in the presence of an acid catalyst and recovering the 3-hydroxymethyl tetrahydrofuran.

2. A process as claimed in claim 1 wherein the alcohol used contain 1 to 4 carbon atoms.

3. A process as claimed in claim 1 wherein the acid catalyst used is a heterogeneous catalyst.

4. A process as claimed in claim 3 wherein the acid catalyst is selected from the group consisting of amberlyst-15, montmorillonite K-10 and Sulphonated Nitro Coal Acid catalyst.

* * * * *